United States Patent

Model et al.

[11] 4,006,162
[45] Feb. 1, 1977

[54] IMINOISOINDOLINONE PIGMENTS

[75] Inventors: Ernst Model, Basel; Jost von der Crone; André Pugin, both of Riehen, all of Switzerland

[73] Assignee: Ciba-Geigy Corporation, Ardsley, N.Y.

[22] Filed: May 6, 1975

[21] Appl. No.: 575,091

[30] Foreign Application Priority Data

May 7, 1974 Switzerland .................. 6181/74

[52] U.S. Cl. .................. 260/325 PH; 8/54.2; 106/23; 106/288 Q; 260/37 P; 260/39 P; 260/42.21; 260/746; 260/315
[51] Int. Cl.$^2$ .................. C07D 209/46
[58] Field of Search .................. 260/325 PH

[56] References Cited

UNITED STATES PATENTS

| | | | |
|---|---|---|---|
| 2,973,358 | 2/1961 | Pugin | 260/325 PH |
| 3,867,404 | 2/1975 | von der Crone et al. | 260/325 PH |

Primary Examiner—Lewis Gotts
Assistant Examiner—S. P. Williams
Attorney, Agent, or Firm—Vincent J. Cavalieri

[57] ABSTRACT

Iminoisoinolinone pigments of the formula

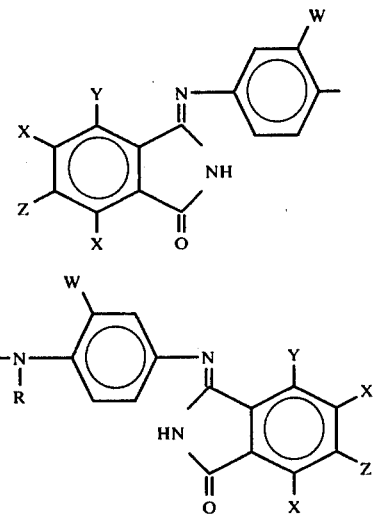

wherein R denotes an alkyl group containing 1–4 C atoms, or an aryl group, the W's denote H atoms or, conjointly denote a direct bond, the X's denote halogen atoms, the Y's and Z's denote halogen atoms, alkoxy or alkylmercapto groups containing 1–6 atoms, cycloalkoxy groups containing 5–6 C atoms, or aralkoxy, aryloxy or arylmercapto groups, which are useful for pigmenting high molecular organic material.

5 Claims, No Drawings

IMINOISOINDOLINONE PIGMENTS

It has been found that valuable, new iminoisoindolinone pigments, in a variety of red shades, of the formula

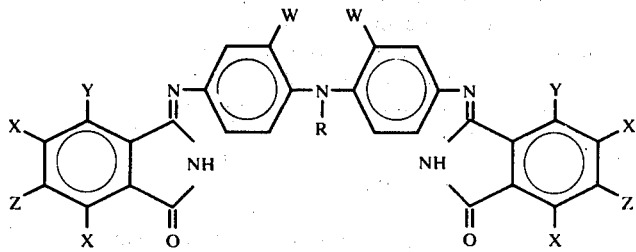

(I)

wherein R denotes an alkyl group containing 1–4 C atoms, or an aryl group, the Ws denote H atoms or, conjointly, denote a direct bond, the Xs denote halogen atoms, Y and Z denote halogen atoms, alkoxy or alkylmercapto groups containing 1–6 C atoms, cycloalkoxy groups containing 5–6 atoms, or aralkoxy, aryloxy or arylmercapto groups, are obtained if an isoindolinone of the formula

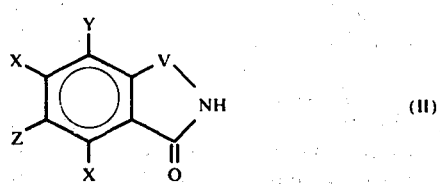

(II)

wherein X, Y and Z have the meaning indicated and V denotes a group of the formula

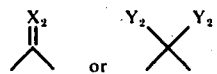

wherein $X_2$ denotes an imino or thio group and the $Y_2$s denote halogen atoms or alkoxy or sec. amino groups, is condensed, in a molar ratio of 2:1, with a diamine or triamine of the formula

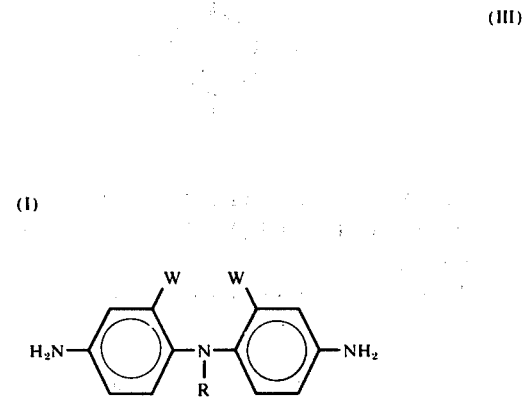

(III)

Compounds of particular interest are those of the formula

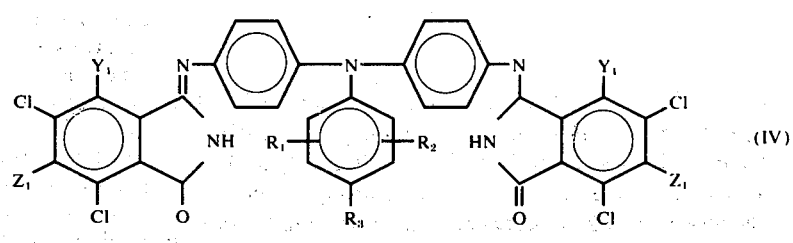

(IV)

wherein $Y_1$ and $Z_1$ denote chlorine atoms or alkoxy groups containing 1–4 C atoms, $R_1$ and $R_2$ denote H or halogen atoms, alkyl or alkoxy groups containing 1–4 C atoms, phenoxy groups or trifluoromethyl groups which are optionally substituted by chlorine atoms or by alkyl or alkoxy groups containing 1–4 C atoms, and $R_3$ denotes a H or halogen atom, an alkyl or alkoxy group containing 1–4 C atoms, or a group of the formula

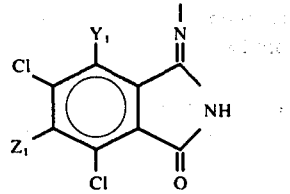

Preferred compounds are also those of the formula

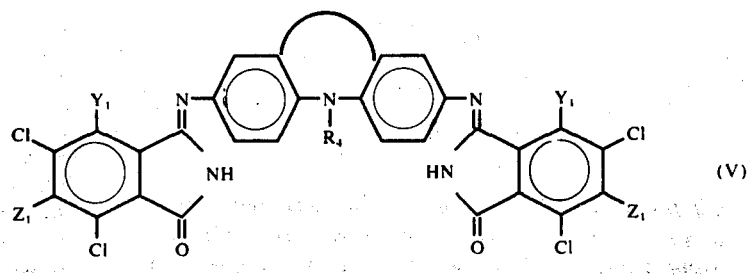

(V)

wherein $Y_1$ and $Z_1$ have the meaning indicated, and $R_4$ denotes an alkyl group containing 1–4 C atoms, or a group of the formula

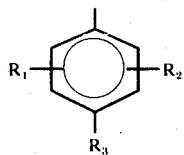

wherein $R_1$, $R_2$ and $R_3$ have the meaning indicated. In the formulae (IV) and (V), $Y_1$ and $Z_1$ preferably denote chlorine atoms.

The starting materials used are preferably isoindolinones of the formula

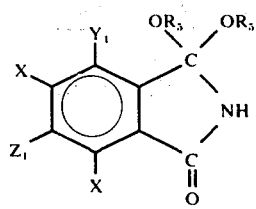

wherein X, $Y_1$ and $Z_1$ have the meaning indicated and $R_5$ denotes an alkyl group containing 1–4 carbon atoms, and particularly those wherein X and $Y_1$ and $Z_1$ denote chlorine atoms. Those starting materials wherein $Y_1$ and $Z_1$ denote chlorine atoms, are known, and those wherein $Y_1$ and $Z_1$ denote alkoxy, cycloalkoxy, aralkoxy, aryloxy, alkylthio or arylthio groups, can be obtained by the process of DOS No. 2,301,863 by reacting an ammonium salt or ester of tetrachloro-o-cyanobenzoic acid in a hydrophilic organic solvent with a compound of the formula $Y_1$Me, wherein $Y_1$ has the abovementioned meaning and Me denotes an alkali metal atom, and, if necessary, esterifying the resulting product and reacting it with a Na alcoholate.

3,3-Dimethoxy-4,5,6,7-tetrachloro-isoindolinone and 3,3-dimethoxy-4,5,6,7-tetrabromo-isoindolinone may be mentioned as examples of isoindolinones.

The isoindolinones mentioned are known compounds.

The diamines used are preferably diamines of the formula

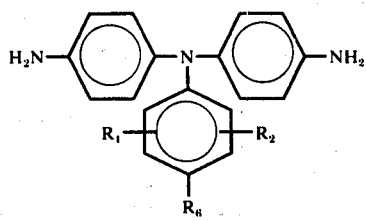

wherein $R_1$ and $R_2$ have the meaning indicated, and $R_6$ denotes a H or halogen atom or an alkyl or alkoxy group containing 1–4 C atoms, or an amino group, or diamines of the formula

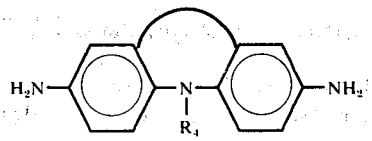

wherein $R_4$ has the meaning indicated.

Some of the diamines mentioned are known compounds. They can be obtained by known processes, for example in accordance with DT-AS 1,793,658 by condensation of 2 mols of p-nitrochlorobenzene with 1 mol of an amine of the formula $RNH_2$ and reduction of the resulting dinitro or trinitro compound.

The condensation of the isoindolinone with the amine is carried out, in part, in the cold, if appropriate whilst warming the intimately mixed components, and particularly advantageously in the presence of inert organic solvents, that is to say organic solvents which do not take part in the reaction.

If 3-imino-, 3-thio or 3,3-bis-sec.amino-4,5,6,7-tetrachloroisoindolin-1-ones or alkali metal salts of the 3,3-dialkoxy-4,5,6,7-tetrachloroisoindolin-1-ones are used as starting materials, it is advantageous to use organic solvents which are miscible with water, for example lower aliphatic alcohols, such as lower alkanols, for example methanol, isopropanol or butanol, lower cyclic ethers, such as dioxane, ethylene glycol monomethyl ether, or lower aliphatic ketones, such as acetone. The condensation takes place in this case even at relatively low temperatures. It is advantageous to carry out the reaction in the presence of base-binding agents; examples of these which should be mentioned are lower fatty acids, which then simultaneously act as a solvent, particularly acetic acid. If 3,3-di-halogeno-4,5,6,7-tetrachloroisoindolin-1-ones are used, organic solvents which are free from hydroxyl groups are preferred, such as hydrocarbons, for example aromatic hydrocarbons, such as benzene, toluene, xylene, tetrahydronaphthalene or diphenyl, or cycloaliphatic hydrocarbons, for example cyclohexane, and also halogenated hydrocarbons, such as aliphatic halogenated hydrocarbons, for example carbon tetrachloride or tetrachloroethylene, or aromatic halogenated hydrocarbons, such as chlorobenzene or dichlorobenzenes and trichlorobenzenes, and also aromatic nitro hydrocarbons, such as nitrobenzenes, ethers and particularly aliphatic ethers, such as dibutyl ether, aromatic ethers, such as diphenyl ether, or cyclic ethers, such as dioxane, and also ketones, such as acetone, or esters, in particular esters of lower fatty acids with lower alkanols, such as ethyl acetate, in the presence of acid-binding agents.

The new pigments are precipitated from the reaction medium immediately after their formation. For certain purposes they can be used direct as crude pigments; but their properties can also be further improved, with particular respect to purity, form and hiding power, by methods which are in themselves known, for example by extraction with organic solvents or by grinding with grinding auxiliaries which can be removed again afterwards, for example salts, or by re-precipitation from alkali. In particular, it is possible to manufacture red pigments which are distinguished by an extraordinary brilliance.

The new colorants are valuable pigments which can be used in a finely dispersed form for pigmenting high molecular organic material, for example cellulose ethers and esters, such as ethylcellulose, acetylcellulose or nitrocellulose, polyamides or polyurethanes or polyesters, natural resins or synthetic resins, for example aminoplasts, especially ureaformaldehyde and melamine-formaldehyde resins, alkyd resins, phenoplasts, polycarbonates, polyolefines, such as polystyrene, polyvinyl chloride, polyethylene, polypropylene, polyacrylonitrile, polyacrylic acid esters, thermoplastic or curable acrylic resins, rubber, casein, silicone and silicone resins, on their own or in mixtures. It is immaterial here whether the high molecular compounds mentioned are present as plastic compositions or melts or in the form of spinning solutions, lacquers or printing inks. Depending on the intended use, it proves advantageous to use the new pigments as toners or in the form of preparations.

The resulting colorations are distinguished by a great depth of colour, high purity of colour shade and good fastness to overlacquering, light and weathering.

In the examples which follow, the parts denote parts by weight.

EXAMPLE 1

A hot solution of 5.5 g of 3,6-diamino-N-ethylcarbazole (prepared by nitrating N-ethylcarbazole and reducing the resulting dinitro compound) in 100 ml of o-dichlorobenzene is poured, while stirring well, into a solution of 17 g of 3,3,4,5,6,7-hexachloro-isoindolin-1-one in 100 ml of o-dichlorobenzene. A red-brown precipitate is immediately formed. The suspension is heated to 150°–160° C and is stirred at this temperature for 2 hours. The virtually insoluble colorant is filtered off at 120° C and is washed with methyl alcohol, acetone and water. After drying, 16 g are obtained of a red pigment which, after being ground by one of the customary methods and incorporated in plastics, gives colorations with outstanding fastness properties.

EXAMPLE 2

16.5 g of 3,4,5,6-tetrachloro-2-cyanobenzoic acid methyl ester are stirred with 55 ml of a 1 N sodium methylate solution in methanol to give a clear solution. The sodium salt of 3,3-dimethoxy-4,5,6,7-tetrachloroisoindolin-1-one is formed. 7.6 g of 4,4'-diamino-2'',6''-dimethyl-triphenylamine (prepared by condensation of p-nitrochlorobenzene with 2,6-dimethylaniline, reaction of the resulting nitrodiphenylamine with a further mol of p-nitrochlorobenzene and reduction of the resulting dinitro compound) are now added, while stirring well, followed, after half an hour, by 100 ml of o-dichlorobenzene. The reaction mixture is stirred overnight at room temperature and is then heated, while methanol distils off, to 100° C. A further 100 ml of o-dichlorobenzene and 20 ml of glacial acetic acid are now added and the temperature is raised to 140°–150° C and is kept there for 2 hours, while stirring well. The precipitated pigment is filtered off at 120° C and is washed with hot methanol, acetone and hot distilled water. After drying, 14 g are obtained of a red pigment which, after being ground by one of the customary methods and incorporated in coloured lacquers, gives brilliant colorations with outstanding fastness properties.

EXAMPLE 3

If, instead of 3,4,5,6-tetrachloro-o-cyanobenzoic acid methyl ester, equimolecular quantities of 3,4,5,6-tetrabromocyanobenzoic acid methyl ester (melting point 122°–124°) are used and the 7.6 g of 4,4'-diamino-2'',6''-dimethyltriphenylamine are replaced by 4.83 g of 4,4',4''-triamino-triphenylamine, and the procedure is as indicated in Example 2, a violet pigment is obtained, the incorporation of which in lacquers and plastics gives colorations of very good fastness to light, weathering and migration.

EXAMPLE 4

If, in Example 3, equimolecular quantities of 3,4,6-trichloro-5-methoxy-o-cyanobenzoic acid methyl ester are used instead of the 3,4,5,6-tetrabromo-2-cyanobenzoic acid methyl ester and the procedure is as indicated, a violet pigment is obtained which, when incorporated in lacquers, exhibits similarly good properties.

EXAMPLES 6 – 33

The table which follows lists further pigments which are obtained if the o-cyanobenzoic acid ester indicated in column II is condensed, in accordance with Example 2, with the diamine or triamine of the formula

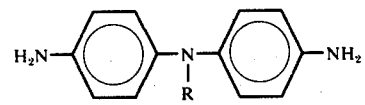

wherein R has the meaning indicated in column III. Column IV indicates the shade of a PVC sheet coloured with the resulting pigments.

| Example | Cyanobenzoic acid ester | R | Shade |
|---|---|---|---|
| 6 | 3,4,5,6-Tetrachloro-2-cyanobenzoic acid methyl ester | Methyl | violet |
| 7 | " | Ethyl | " |
| 8 | " | Phenyl | red |
| 9 | " | 2-Methylphenyl | scarlet |
| 10 | " | 3-Methylphenyl | red |
| 11 | " | 4-Methylphenyl | red |
| 12 | " | 2-Methoxyphenyl | red |
| 13 | " | 3-Methoxyphenyl | orange |
| 14 | " | 4-Methoxyphenyl | violet |
| 15 | " | 2-Chlorophenyl | scarlet |
| 16 | " | 3-Chlorophenyl | " |
| 17 | " | 4-Chlorophenyl | red |
| 18 | " | 2,4-Dimethylphenyl | " |
| 19 | " | 3,4-Dimethylphenyl | " |
| 20 | " | 3,5-Dimethylphenyl | " |
| 21 | " | 3-Trifluoromethylphenyl | orange |
| 22 | " | 2,4-Dichlorophenyl | orange |
| 23 | " | 2,5-Dichlorophenyl | scarlet |
| 24 | " | 3,4-Dichlorophenyl | orange |
| 25 | " | 2-Chloro-5-trifluorophenyl | " |

-continued

| Example | Cyanobenzoic acid ester | R | Shade |
| --- | --- | --- | --- |
| 26 | '' | 4-Chloro-3-trifluorophenyl | scarlet |
| 27 | '' | 2,4,6-Trimethylphenyl | red |
| 28 | '' | 2,6-Dimethyl-4-bromophenyl | '' |
| 29 | '' | 2-Bromophenyl | red |
| 30 | '' | 1-Naphthyl | '' |
| 31 | '' | (structure shown) | violet |
| 32 | 3,4,6-Trichloro-5-methoxy-2-cyanobenzoic acid methyl ester | Phenyl | orange |
| 33 | '' | 2,6-Dimethylphenyl | orange |

EXAMPLES 34 – 37

The pigments listed in the table which follows are obtained if the o-cyanobenzoic acid ester indicated in column II is condensed, in accordance with Example 2, with the diamine or triamine of the formula

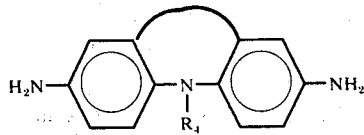

wherein $R_4$ has the meaning indicated in column III. Column IV indicates the shade of a PVC sheet coloured with the resulting pigment.

| Example | Cyanobenzoic acid ester | $R_4$ | Shade |
| --- | --- | --- | --- |
| 34 | 3,4,5,6-Tetrachloro-2-cyanobenzoic acid methyl ester | Ethyl | red |
| 35 | '' | (structure shown) | violet |
| 36 | 3,4,6-Trichloro-5-methoxy-2-cyanobenzoic acid ester | Ethyl | scarlet |
| 37 | 4,6-Dichloro-3,5-dimethoxy-2-cyanobenzoic acid methyl ester | '' | orange |

EXAMPLE 38

2 g of the pigment prepared according to Example 34 are mixed and ground on a triple roll mill with 36 g of hydrated aluminium oxide, 60 g of linseed oil varnish of average viscosity and 0.2 g of cobalt linoleate. The red prints produced with this colouring paste have a deep colour and are fast to light.

EXAMPLE 39

0.6 g of the pigment prepared in accordance with Example 1 are mixed with 67 g of polyvinyl chloride, 33 g of dioctyl phthalate, 2 g of dibutyl-tin dilaurate and 2 g of titanium oxide and the mixture is milled for 15 minutes on a triple roll mill. The yellowish-tinged red polyvinyl chloride sheets thus produced are distinguished by outstanding fastness to migration, heat and light.

EXAMPLE 40

10 g of titanium oxide and 2 g of the pigment prepared in accordance with Example 2 are ground for 48 hours in a ball mill with 88 g of a mixture of 26.4 g of coconut alkyd resin, 24.0 g of melamine-formaldehyde resin (50% solids content), 8.8 g of ethylene glycol monomethyl ether and 28.8 g of xylene.

If this lacquer is sprayed onto an aluminium foil, pre-dried for 30 minutes at room temperature and then stoved for 30 minutes at 120° C, a red lacquering is obtained which is distinguished by good brilliance and depth of colour and by very good fastness to light and weathering.

What we claim is:
1. An iminoisoindolinone pigment of the formula

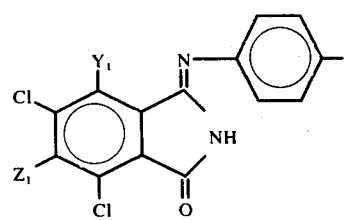

-continued

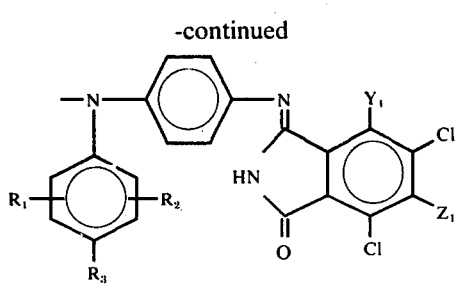

wherein $Y_1$ and $Z_1$ denote chloro, alkoxy containing 1 to 4 carbon atoms, $R_1$ and $R_2$ denote H, halogen, alkyl containing 1 to 4 carbon atoms, alkoxy containing 1 to 4 carbon atoms, phenoxy, phenoxy optionally substituted by chloro, alkyl containing 1 to 4 carbon atoms, or alkoxy containing 1 to 4 carbon atoms, or trifluoromethyl, $R_3$ denotes H, halogen, alkyl containing 1 to 4 carbon atoms, alkoxy containing 1 to 4 carbon atoms, or a group of the formula

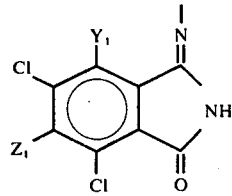

2. Iminoisoindolinone pigment according to claim 1, wherein $Y_1$ and $Z_1$ denote chlorine atoms.

3. A pigment of the formula

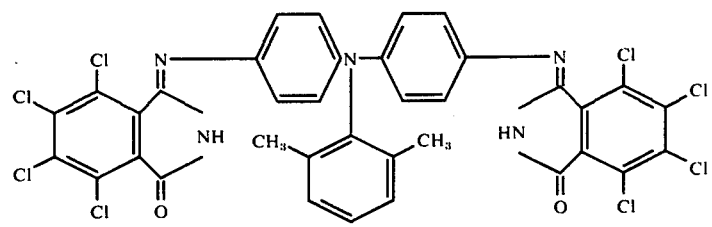

4. A pigment of the formula

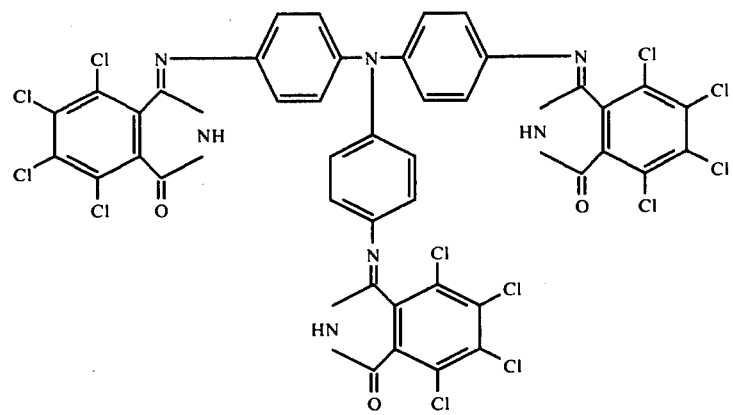

5. A pigment of the formula

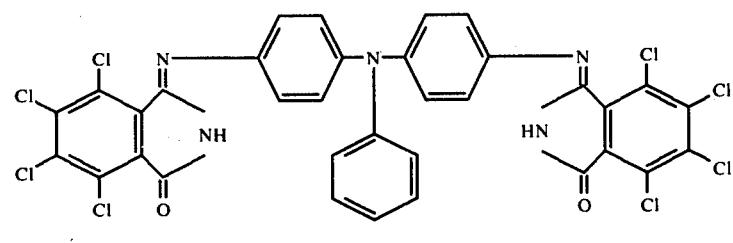

* * * * *